United States Patent [19]

Badorc et al.

[11] Patent Number: 5,252,749
[45] Date of Patent: Oct. 12, 1993

[54] ETHERS OF THIENOCYCLOPENTANONE OXIMES, THEIR PREPARATION AND PHARMACEUTICAL COMPOSITIONS CONTAINING THEM

[75] Inventors: Alain Badorc; Jean Courregelongue, both of Portet; Daniel Ducros, St. Orens de Gameville; Daniel Frehel, Toulouse, all of France; Antonina Giudice, Milan, Italy; Claudine Serradeil-Legal, Toulosan, France

[73] Assignee: Elf Sanofi, Paris, France

[21] Appl. No.: 954,530

[22] Filed: Sep. 23, 1992

[30] Foreign Application Priority Data

Sep. 25, 1991 [FR] France .................. 91 11822

[51] Int. Cl.$^5$ .................. C07D 333/78; A61K 31/15; A61K 31/38
[52] U.S. Cl. .................. 549/51; 549/52; 549/54; 549/55; 549/56; 549/57; 546/202; 546/274; 544/146
[58] Field of Search .................. 549/57, 51, 52, 54, 549/55, 56; 514/443, 233.5, 324, 337

[56] References Cited

U.S. PATENT DOCUMENTS

| | | | |
|---|---|---|---|
| 3,301,874 | 1/1967 | Sam | 549/51 |
| 4,154,740 | 5/1979 | Asato | 549/51 |
| 4,649,153 | 3/1987 | Ferrand et al. | 549/57 X |

FOREIGN PATENT DOCUMENTS 2066808  7/1981  United Kingdom .................. 549/57

OTHER PUBLICATIONS

N. Ake Jonsson et al., "Pharmacologically active derivatives of geminally dialykylated indenes and indans", Chemical Abstracts, vol. 90, No. 25, Jun. 18, 1979, Abstract No. 203744B.

*Primary Examiner*—Marianne M. Cintins
*Assistant Examiner*—Michael B. Hydorn

[57] ABSTRACT

The compounds of the invention having the formula:

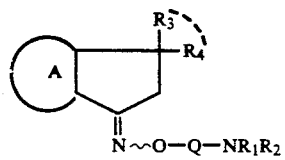

in which: A, which is a ring condensed with cyclopentane, represents a substituted or unsubstituted thiophene ring, Q represents an alkylene chain, $R_1$ and $R_2$ each represent H or an alkyl, or they form, with the nitrogen atom to which they are linked, a saturated nitrogenous heterocyclic ring containing 5 to 7 atoms, $R_3$ and $R_4$ each represent H, alkyl, cycloalkyl, trifluoromethyl or an optionally substituted phenyl, thienyl or furyl group or $R_3$ and $R_4$ together form a ($C_5$–$C_8$) cycloalkyl, as well as their addition salts with an acid and their quaternary ammonium derivatives.

They can be used as medicines.

16 Claims, No Drawings

ETHERS OF THIENOCYCLOPENTANONE OXIMES, THEIR PREPARATION AND PHARMACEUTICAL COMPOSITIONS CONTAINING THEM

The present invention relates to the ethers of thienocyclopentanone oximes, as well as to processes for their preparation and to their application as medicines.

Ethers of oximes of condensed cyclopentanone of formula:

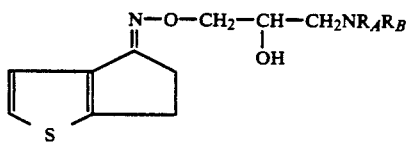

were described in EP-A-031266 as exhibiting a $\beta$-receptor inhibitory activity; the compounds of the present invention do not have this pharmacological activity but bind to biological receptors for serotonin; their therapeutic activities will therefore not be comparable to those of the known compounds.

The compounds of the invention correspond to the formula:

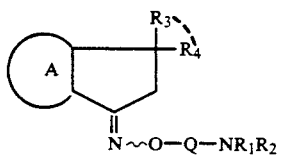

in which:
A, which is a ring condensed with cyclopentane, represents an unsubstituted or monosubstituted or polysubstituted thiophene nucleus; the substituents can be chosen from the alkyl, alkoxy, halo (especially Cl or Br), nitro, hydroxyl and trifluoromethyl groups, Q represents an alkylene chain, $R_1$ and $R_2$, which are identical or different, each represent H, an alkyl or pyridylethyl or they form, with the nitrogen atom to which they are linked, a saturated nitrogenous heterocyclic ring containing 5 to 7 atoms, optionally containing a second heteroatom O, S or N, the latter being optionally substituted with an alkyl or a phenyl, $R_3$ and $R_4$, which are identical or different, each represent H, alkyl, cycloalkyl, a trifluoromethyl group or a phenyl, thienyl or furyl aromatic group, optionally substituted with one or more alkyl, alkoxy, halo (especially F, Cl or Br), trifluoromethyl, trifluoromethoxy, hydroxyl, cyano, carboxyl, nitro, alkoxycarbonyl, carbamoyl, or N-alkyl- or N,N-dialkylcarbamoyl groups, or $R_3$ and $R_4$, together with the carbon atom to which they are bound, form a ($C_5$-$C_8$) cycloalkyl (spiro derivatives);

their addition salts with an acid and their quaternary ammonium derivatives are also part of the invention.

The compounds can exist in one of the E or Z configurations around the C=N—double bond of the oxime, which is expressed in the C=N O notation; each of the geometric isomers of the compounds of formula I and their mixtures in any proportion are part of the invention; additionally, when $R_3$ is different from $R_4$, these compounds contain at least one asymmetric carbon and each of the dextrorotatory or laevorotatory stereoisomers of formula I and the mixtures, in any proportion, of the 4 types of isomers of a compound of formula I are also part of the invention.

A quaternary ammonium compound is a compound of formula:

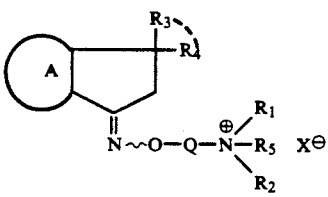

in which $R_5$ represents an alkyl group and X a halogen atom, especially Cl and Br, or $SO_4^{2-}$ or $NO_3$.

The alkyl, alkoxy, and alkylene groups can be linear or branched; the alkyl groups are $C_1$-$C_4$, as well as the alkoxy and alkylene groups; the cycloalkyl groups are $C_4$-$C_8$; the alkylene groups are $C_2$-$C_4$. There may be mentioned, among the heterocyclic groups represented by $NR_1R_2$, the morpholino, thiomorpholino, piperidino, pyrrolidinyl, 1-piperazinyl and 4-alkyl-1-piperazinyl groups.

In all the compounds of formula I, a preferred group consists of the compounds for which A represents unsubstituted thiophene, Q is $CH_2CH_2$, and $R_1$ and $R_2$ represent H or alkyl, particularly methyl.

There may be mentioned, among the particularly preferred compounds:
4-(2-chlorophenyl)thieno[2,3-b]cyclopentan-6-one oxime O-(2-{N,N-dimethylamino}ethyl) ether
4-(2-bromophenyl)thieno[2,3-b]cyclopentan-6-one oxime O-(2-{N,N-dimethylamino}ethyl) ether
4-(2-methoxyphenyl)thieno[2,3-b]cyclopentan-6-one oxime O-(2-{N,N-dimethylamino}ethyl) ether
4-(4-methylphenyl)thieno[2,3-b]cyclopentan-6-one oxime O-(2-{N,N-dimethylamino}ethyl) ether
4-methyl-4-(2-chlorophenyl)thieno[2,3-b]cyclopentan-6-one oxime O-(2-{N,N-dimethylamino}ethyl) ether
4-methyl-4-(2-methoxyphenyl)thieno[2,3-b]cyclopentan-6-one oxime O-(2-{N,N-dimethylamino}ethyl) ether
4,4-dimethylthieno[2,3-b]cyclopentan-6-one oxime O-(2-{N,N-dimethylamino}ethyl) ether
4-(2-hydroxyphenyl)thieno[2,3-b]cyclopentan-6-one oxime O-(2-{N,N-dimethylamino}ethyl) ether
spiro(cyclopentane-1,4'-thieno[2',3'-b]cyclopentan-6'-one) oxime O-(2-{N,N-dimethylamino}ethyl) ether
4-methyl-4-(3-chlorophenyl)thieno[2,3-b]cyclopentan-6-one oxime O-(2-{N,N-dimethylamino}ethyl) ether
spiro(cyclohexane-1,4'-thieno[2',3'-b]cyclopentan-6'-one) oxime O-(2-{N,N-dimethylamino}ethyl) ether,
4-methyl-4-(2-methylphenyl)thieno[2,3-b]cyclopentan-6-one oxime O-(2-{N,N-dimethylamino}ethyl)ether
4-methyl-4-2-bromophenyl thieno[2,3-b]cyclopentan-6-one oxime O-(2-{N,N-dimethylamino}ethyl)ether
and more particularly their Z isomers.

The processes for preparing the compounds of formula I are also within the invention.

These compounds can be prepared: from the ketones of formula

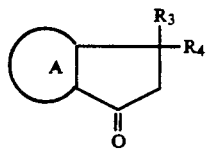
II in which A, $R_3$ and $R_4$ have the same meanings as in formula I, by reacting them with:
1) a hydroxylamine, optionally substituted on the oxygen: namely
the hydroxylamine $$H_2NO-Q-NR_1R_2 \quad III$$

in order to obtain the compound of formula I directly or the hydroxylamine $$H_2NO-Q-X \quad IV$$

in which X represents a halogen atom, especially Br, a quaternary ammonium group or a sulphate group, in order to obtain the compound

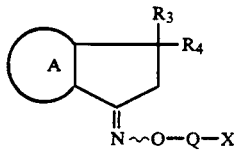
V which is reacted with an amine $HNR_1R_2$ or $NR_1R_2R_5$ according to the compound of formula I required,
or the hydroxylamine $H_2NOH$
in order to obtain the oxime of formula

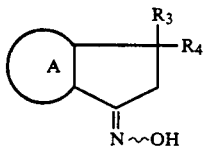
VI which is substituted at the oxygen by reacting it with $Y-Q-NR_1R_2$ in order to obtain a compound of the formula I or by reacting it with $Y-Q-X$ in order to obtain a compound of formula V which will then be converted to the compound of formula I, or else 2) an oxime ether of low molecular weight, of formula

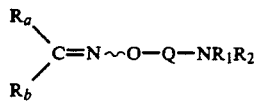
VII in which $R_a$ and $R_b$ are $(C_1-C_4)$alkyls.

In the preceding formulae, $Q_1$, $R_1$, $R_2$, $R_3$, $R_4$ and $R_5$ have the same meanings as in the formula I and Y represents a halogen atom or a sulphate group.

In the cases where $R_1$ or $R_2$ is different from H, it is possible to prepare the compound in which $R_1$ and $R_2$ are H and to substitute it using a usual process, for example by reacting it with an alkyl halide.

The salts, which are within the invention, are prepared in a manner known per se, by reacting the selected acid with the amine of formula I in solution, for example in acetone or an alcohol; the salts precipitate spontaneously in the reaction medium or are precipitated by addition of a non-solvent or by evaporation of the solvent. The acid will be selected from the pharmaceutically acceptable acids, well known to those skilled in the art, in order to prepare a medicine, or from the acids which are useful for facilitating the purification of the compounds of formula I or of making it possible to isolate a geometric isomer or an optical isomer, for an optically active acid.

The quaternary ammonium compounds can be prepared directly or from the corresponding amines $NR_1R_2$ by reacting them with $R_5-X$.

It is known that, according to the type of process used, the operating conditions and the structure of the ketone II, different relative proportions of the 2 geometric isomers of the oxime can be obtained and the person skilled in the art will choose from the various preparation possibilities, with the help of a few preliminary trials, the one will make it possible to obtain the required proportion of isomers or optionally a pure isomer.

It was observed that the geometric isomers of the compounds of formula V were able to be easily separated by chromatography on a silica column, and it is preferable, in order to obtain a practically pure Z or E isomer of a compound of formula I, to prepare this compound via the intermediary of V (X=Br).

Nevertheless, other methods can be suitable, such as separation at the stage of the oxime VI, after an optional enrichment in the required isomer by isomerisation around the C=N double bond by carrying out an acidic or even basic treatment of VI, according to known techniques.

The two geometric isomers will also be able to be separated by recrystallisation of a suitable salt of the compound of formula I, or optionally by a high performance liquid chromatography of the compound of formula I.

In order to separate the two enantiomers of formula I which exist when $R_3$ is different from $R_4$, it will be possible:

either to carry out, in a conventional way, fractional recrystallisations of an addition salt of the compound of formula I, preferably the salt of only one of the two geometric isomers, with a pure enantiomer of an optically active acid, or to separate the two enantiomers of the ketones of formula II before preparing the compounds of formula I by one of the abovementioned processes, by carrying out a fractional crystallisation of a derivative of II containing a second asymmetric carbon in order to obtain a pure diastereoisomer from which the ketone can be regenerated; there may be mentioned, among the derivatives of II, the acetals or the oxime ethers, containing an amine group or an acid group converted to salts with an optically active acid or base respectively, two groups which are known to give the ketone by hydrolysis in aqueous medium.

The hydroxylamine ethers III and IV are known compounds or they can be prepared by analogy to known methods; for example, they are prepared by hydrolysis in aqueous acidic medium of the derivatives of formula VII in which $R_a$ and $R_b$ are $(C_1-C_3)$ alkyl groups or phenyl groups or else by reacting hydrazine or a primary amine with the phthalimides of formula:

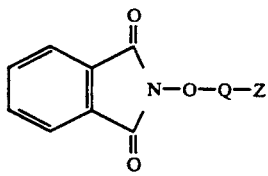

in which Z represents $NR_1R_2$ or X as applicable, and Q, $R_1$ and $R_2$ are as defined above.

The hydroxylamine ethers are purified by recrystallisation of their salts with an acid, especially a strong inorganic acid, for example by recrystallisation of their hydrochlorides, or, for the compounds of formula III, by distillation.

In order to obtain a compound of formula I or V, the hydroxylamine ether of formula III or IV, preferably in the salt form, is reacted with the ketone of the formula II in solution in an alcohol, generally at the reflux temperature of the solvent; the preparation can also be carried out in any other inert solvent or in a mixture of alcohol and pyridine or of pyridine and acetic acid.

In order to obtain a compound of formula V in which X is a quaternary ammonium group, the amine $NR_1R_2R_5$ is reacted with the compound V in which X represents a halogen atom.

The oxime VI of the ketone II can be prepared in a known way by reacting a salt of the hydroxylamine with the ketone in solution, in the presence of an acid or a base, and, for example, in an alcohol in the presence of an alkali metal hydroxide, sodium acetate or pyridine or even in acetic acid or in pyridine; an excess of hydroxylamine is generally used. The relative percentages of the two geometric isomers obtained can be substantially modified by the choice of the operating conditions.

The alkylation of the oxime VI can be carried out by reacting a compound of formula

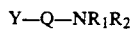

in a basic medium under various well-known operating conditions, for example in a polar aprotic solvent such as dimethylformamide, with at least one equivalent of an alkali metal alcoholate, of a hydroxide or of an alkali metal carbonate, or else in an alcohol with at least one equivalent of an alkali metal alcoholate or of an alkali metal hydroxide or even in a mixture of pyridine and alcohol or else in a hydrocarbon solvent such as benzene or toluene in the presence, for example, of an alkali metal carbonate.

The reaction of a compound of formula VII with the ketone II can be carried out in an alcoholic solvent such as butanol, optionally in the presence of water, at the reflux temperature of the solvent, in acid medium and, preferably, the ketone $R_aR_bC=O$ formed is simultaneously removed by distillation; if the compound of formula VII is not introduced into the reaction medium in the form of a salt of the amine, a quantity of acid sufficient to form this salt is introduced into the medium, in addition to the quantity necessary for the transoximation reaction; the latter is not critical but, in the case where the acid is an acid which can be removed during the distillation of the ketone, especially hydrochloric acid, a large excess of it is introduced; sulphuric acid, para-toluenesulphonic acid and methanesulphonic acid will be used in lesser quantities.

It is known that the alkylation of the oximes can be carried out either on the oxygen or on the nitrogen, giving, in the latter case, nitrones; the latter are not part of the invention and the use of a process which would lead to the formation of not insignificant quantities of nitrone will be avoided. Likewise, when it is appropriate to isolate only one of the two geometric enantiomers, the preferred process will be the one which will allow to isolate, with the best yield and/or the simplest procedure, the isomer required; this preferable process will depend on A, Q, $R_1$, $R_2$, $R_3$ and $R_4$ and the person skilled in the art will determine it via usual experimentation. When it is wished to isolate only a single one of the enantiomers, it will be generally preferable to carry out this separation for the ketone, as the subsequent oximation does not bring about racemisation, or for a single geometric isomer in order to facilitate the recrystallisations and the separation of the diastereoisomers.

The ketones of formula (II) are known or are prepared by analogy with known processes.

Preferably, they are prepared by applying the reaction scheme (a) below

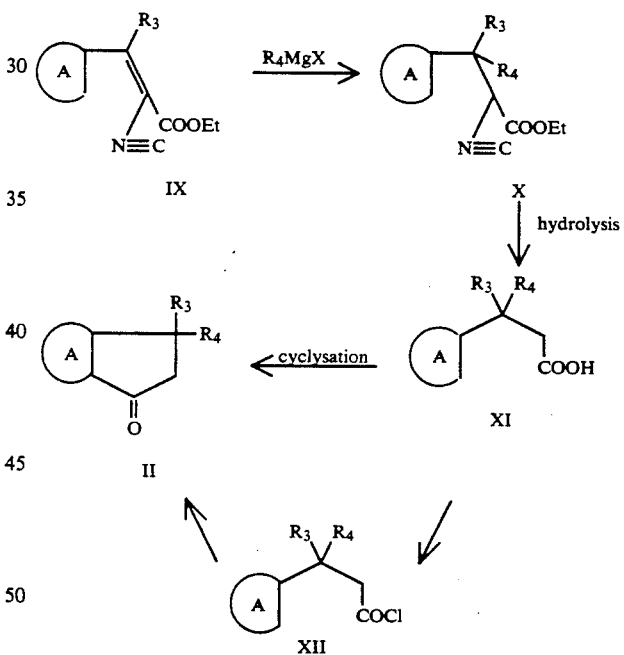

in which X represents a halogen atom and A, $R_3$ and $R_4$ have the same means as in I.

The principle of this process was described by P. Stanetty in J. Chem. Research (M) 1043 (1981) for the preparation of the compound of formula

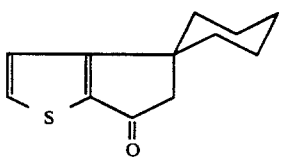

in accordance with the reaction scheme (b)

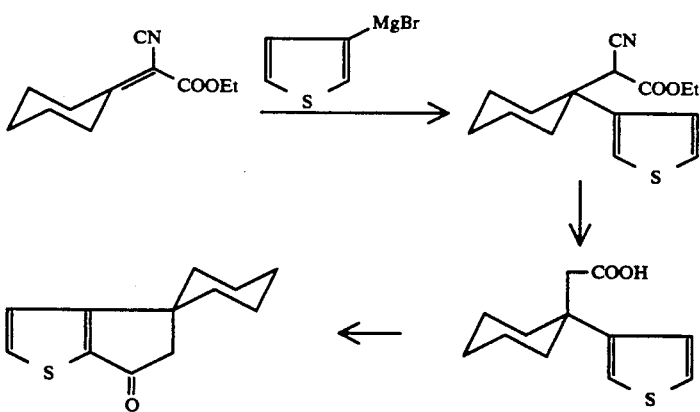

The compounds IX can be prepared from the ketones XIII by a method known as Knoevenagel condensation described, for example, in Org. Reactions 15, 204 (1967), according to the reaction scheme (c)

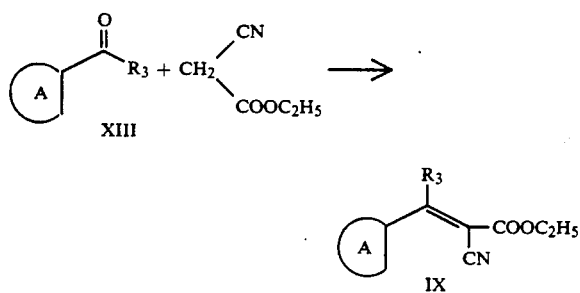

in the presence of acetic acid and ammonium acetate.

The cyclisation of the acid XI can be carried out directly in pure polyphosphoric acid or in suspension in an inert solvent such as toluene or xylene at temperatures ranging from 40° C. to 120° C.

It can also be done via the intermediary of the acid chloride XII in the presence of a Lewis acid such as AlCl₃ or SnCl₄ in a solvent commonly used for Friedel-Crafts reactions, such as carbon disulphide, as described in J. Org. Chem. 32, 1226 (1967).

When the substituents on the heterocyclic ring A or R₃ do not make it possible to use an organomagnesium compound R₄MgX, the ketones II can be obtained by cyclisation of the corresponding chalcones of formula XIV;

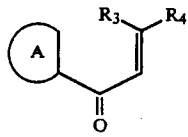

in phosphoric acid at a temperature of between 40° C. and 120° C., optionally in a solvent such as xylene, according to a process described, for example, in J. Heterocyclic Chem. 18, 727 (1981) and Act. Chem. Scand. 20, 1577 (1966) for compounds of formula:

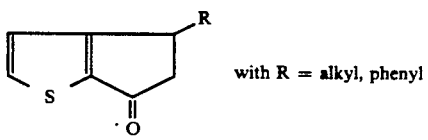

with R = alkyl, phenyl

The chalcones XIV in which R₃ is H can be obtained by reacting the aldehyde R₄CHO with the methyl ketone:

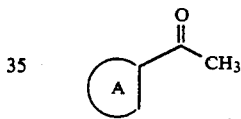

The other chalcones XIV can be prepared by acylation of the heterocyclic ring A with the acrylic acid XV according to the reaction scheme (d):

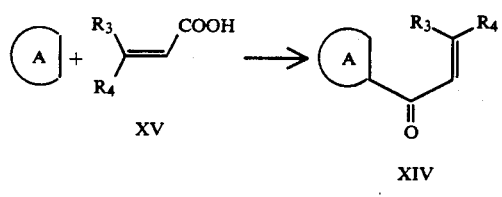

for example, in a solvent such as dichloromethane in the presence of polyphosphoric acid as described in Act. Chem. Scand. 20, 1577 (1966) or by Friedel-Crafts reaction between the acid chloride of XV and the heterocyclic ring A in the presence of a Lewis acid such as AlCl₃ or SnCl₄.

The acrylic acids XV are commercially available or are prepared, for example, by the Wadworth-Emmons method described in Advances in Organic Chemistry 1, 43, (1960), according to the reaction scheme (e):

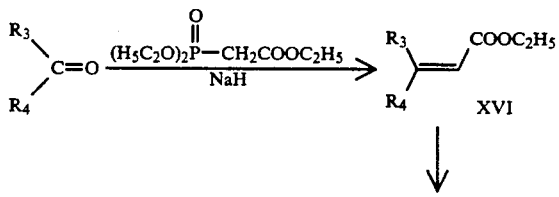

-continued

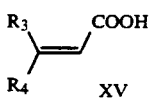

XV

The compounds of the invention and their salts bind to the biological receptors for serotonin (or 5HT), which are present in man especially in the brain, the spleen, blood platelets and the gastrointestinal tract; this amine regulates and controls many physiological activities and it has been shown that it was involved in various pathologies including hypertension and certain vascular disorders, in psychiatric disorders including depression, anxiety and memory disorders, in migraine, in anorexia or obesity; it also plays a role in the perception of pain.

The presence has been demonstrated, in man and mammals, of various types of receptors for serotonin, 5HT, $5HT_2$ and $5HT_3$, according to the classification of P. B. Bradley mentioned in Neuropharmacology 25 (6), 563-576 (1986), as well as, since this date, $5HT_4$ and sub-types of $5HT_1$: $5HT_{1A}$, $5HT_{1B}$, $5HT_{1C}$ and $5HT_{1D}$. These types of receptors were identified by studying the selective binding of various radiolabelled molecules in place of serotonin in various tissues; it has also been determined, with more or less precision according to whether or not there was available an agonist or antagonist which was selective for a receptor type, to which receptor class certain of the physiological activities of serotonin corresponded.

Thus, it was shown that the antagonists of serotonin at the $5HT_3$ receptors reduce nausea and vomiting due to radiotherapies and to anticancer chemotherapies; these antagonists are also currently being clinically studied as anxiolytic agents and in the treatment of schizophrenia or cognitive disorders, and during weaning from drug addiction—as mentioned in TIPS, April 89, p. 127-129 or else in the treatment of certain intestinal motility disorders, as stimulants.

The type $5HT_{1D}$ receptors, which differ little from the type $5HT_{1B}$ which is only present in certain animal species, were identified more recently, and agonists or antagonists which are strictly selective for these receptors have not yet been found; however, for example, sumatriptan (also called GR 43175), which is a powerful agonist of the $5HT_{1D}$ receptor and a weak agonist of the $5HT_{1A}$ receptor, as is mentioned in Headache 29, 420-422, July 1989, has shown a marked antimigraine activity in man, probably due to its effect on the carotid and cerebral circulations; moreover, 5-methoxy-3-(1,2,3,6-tetrahydro-4-pyridyl)-1H-indole (or RU 24969) is being studied as an antidepressant.

The compounds according to the invention bind to the $5HT_3$ and $5HT_{1D}$, or $5HT_{1B}$, receptors to the exclusion of the other receptors of serotonin currently identified; according to their structure and their configuration, they can be more or less specific to the $5HT_3$ receptors or to the $5HT_{1D}$ and $5HT_{1B}$ receptors. They might thus be used in human therapy for the preventive or curative treatment of disorders due, depending on the individual case, to a hyperstimulation of the $5HT_3$ receptors or a hypostimulation of the $5HT_{1D}$ receptors by endogenous serotonin, with a minimum of secondary effects when the products are specific to the receptor type.

Another subject matter of the invention are pharmaceutical compositions containing at least one of the isomers of compounds of formula I or of their salts with pharmaceutically acceptable acids as active ingredient in combination with the usual carriers.

They may be administered orally or transdermally or by injection, in the usual way, one or several times per day, at doses which will depend of the structure of the compound, of the administration route, of the nature and of the intensity of the illness. The unit dosis will contain, besides the vehicles conventionally used, for administration by the oral route, generally from 10 to 500 mg of a compound according to the invention, while the injectable dosis will contain from 1 mg to 20 mg.

It has been shown that one of the geometric isomers of each compound of formula I, namely the Z isomer, has an affinity for the $5HT_{1D}$ receptor which is distinctly more marked than its homologue, whose affinity is generally too weak to have a physiological implication at therapeutically acceptable doses, whatever A, $R_3$, $R_4$, Q and $NR_1R_2$ may be; moreover, this geometric isomer Z has practically no affinity for the $5HT_3$ receptor, contrary to its E homologue.

Moreover, as is frequently observed, the two enantiomers corresponding to the asymmetric carbon to which $R_3$ and $R_4$ are bound can exhibit differences in the intensity of their pharmacological activity and, possibly, differences in toxicity.

The affinity of the compounds for the $5HT_{1D}$ receptors was studied, in vitro, on membrane preparations of bovine caudate nuclei according to a method, the principle of which is described in J. Neuroscience 7 (3), 894-903 (1987), which consists in measuring the displacement of tritiated serotonin from its receptors by the compound to be tested introduced at increasing concentrations in the medium; under these conditions, the concentration which inhibits 50% of the binding of the tritiated compound (or $IC_{50}$) is approximately 100 nM for sumatriptan and from 10 nM to 200 nM for the Z geometric isomers of the compounds of formula I; the most active compounds studied are those for which, Q is $CH_2CH_2$, $R_1$ and $R_2$ are $CH_3$ and $R_3$ is H or $CH_3$ with $R_4$ being phenyl, optionally substituted at the ortho position, especially with a halogen, such as Cl or Br, or with $OCH_3$.

These compounds are also active in vivo in psychopharmacological tests intended to reveal an antidepressive or antiaggressive activity; in contrary to GR 43175, these compounds cross the hematoencephalic barrier.

The antagonist activity of serotonin on the $5HT_3$ receptors for the compounds of the invention was studied in vivo in rats, according to a method described in J. Pharm. Pharmacol. 40, 301-302 (1988), which consists in studying the Bezold-Jarisch reflex; the dose which inhibits 50% of the serotonin activity ($ID_{50}$) in this test is approximately 1 μg/kg for ICS 205-930, 400 μg/kg for metoclopramide and 0.25 μg/kg for zacopride, compounds studied in the abovementioned article. The E geometric isomers of the compounds of formula I have $ID_{50}$ values of between 1 and 250 μg/kg; the Z isomers have little or no activity.

Examples of embodiments of the invention are described below.

The melting points mentioned are instantaneous melting points; the elementary analysis and the infrared and nuclear magnetic resonance spectra are correct; the specific optical rotations were measured for the D line of sodium at 20° C. at the concentrations indicated, expressed as g/100 ml; the thin layer chromatographies were carried out on common silica gel plates, marketed, for example, by Merck. H-oxalate and H-fumarate means an acid salt of oxalic or fumaric acid in which one molecule of diacid is combined with one molecule of amine.

The preparation of some starting compounds is first of all recalled, by way of indication only.

PREPARATION OF CHALCONES

Procedure

A) 2-(2-bromophenyl)vinylene 2-thienyl ketone formula XIV: A=2-thienyl; $R_3$=H; $R_4$=2-bromophenyl 2.04 g (0.016 mole) of 2-acetylthiophene are dissolved in 10 ml of ethanol. 3 g (0.016 mole) of 2-bromobenzaldehyde and 0.2 g of potassium hydroxide pellets are added to the solution. The mixture is poured into an ultrasonic vessel and is left for 30 minutes at room temperature. The reaction mixture is poured into 50 ml of ethyl acetate which is extracted with 20 ml of salted water. The aqueous phase is separated and the organic phases are dried over anhydrous sodium sulphate. Evaporation leaves an oil which is purified by flash chromatography on a silica column (eluent: toluene).

Yield: 70%.
M.p.=52° C.

B) 2-(2-chlorophenyl)vinylene 2-thienyl ketone formula XIV: A=2-thienyl; $R_3$=H; $R_4$=2-chlorophenyl Introduce 289.2 g of 2-chlorobenzaldehyde, 252.34 g of 2-acetylthiophene and 120 ml of acetic acid into a 2 l round bottom flask under a nitrogen atmosphere. Stir and add 198 ml of piperidine over 10 minutes. The temperature of the reaction mixture rises to 60° C. Heat progressively from 60° C. to 115°-120° C. over one hour. Maintain at this temperature for 30 minutes and then distil the volatile products under reduced pressure (130 Pa) until piperidinium acetate appears in the condenser.

Cool at 50°-60° C. and add 2.5 l of isopropyl ether. Wash with 2.5 l of water, 2.5 l of N hydrochloric acid and 2 times 2 l of water. Dry the organic phase over sodium sulphate. Progressively concentrate the isopropyl ether, under reduced pressure, to a volume of approximately 1.5 l. The chalcone partially crystallises. Cool at approximately 0° C. for 12 hours. Filter. Remoisten the precipitate in the minimum of petroleum ether. Filter, drain and dry, under reduced pressure, at 35° C.

343 g of the required product are thus obtained which melts at 61° C.

The compounds of Table 1 were prepared by applying one of the methods described in A and B

TABLE 1

A—C—CH=CH—$R_3$  (XIV: $R_4$ = H)
 ‖
 O

| A—C—  ‖  O | $R_3$ | M.p. (°C.) B.p. (p) | Process according to |
|---|---|---|---|
| 2-thienyl-C(O)- | 2-Cl-phenyl | 61 | A |
| 2-thienyl-C(O)- | 2-NO₂-phenyl | 134 | B |
| 2-thienyl-C(O)- | 2-CF₃-phenyl | 86 | A |
| 2-thienyl-C(O)- | 3-Cl-phenyl | 88 | B |
| 2-thienyl-C(O)- | 4-Cl-phenyl | 113 | B |
| 2-thienyl-C(O)- | 3-CH₃-phenyl | 56 | A |

TABLE 1-continued $$A-\underset{\underset{O}{\|}}{C}-CH=CH-R_3 \quad (XIV: R_4 = H)$$

| $A-\underset{\underset{O}{\|}}{C}-$ | $R_3$ | M.p. (°C.) B.p. (p) | Process according to |
|---|---|---|---|
| 2-thienyl-C(O)- | 2-methylphenyl | 89 | B |
| 2-thienyl-C(O)- | phenyl | 82 | B |
| 2-thienyl-C(O)- | 2-bromophenyl | 52 | B |
| 2-thienyl-C(O)- | —C(CH₃)₃ | Oil* | B |
| 2-thienyl-C(O)- | 3-nitrophenyl | 148 | B |
| 2-thienyl-C(O)- | 2-methoxyphenyl | 71 | B |
| 2-thienyl-C(O)- | —CH₃ | B.p. = 134° C. (2MPa) | B |
| 5-methyl-2-thienyl-C(O)- | 2-chlorophenyl | 89 | A |
| 5-chloro-2-thienyl-C(O)- | 2-chlorophenyl | 138 | A |
| 5-methyl-2-thienyl-C(O)- | 2-bromophenyl | 75 | A |

TABLE 1-continued $$A-\underset{\underset{O}{\|}}{C}-CH=CH-R_3 \quad (XIV: R_4 = H)$$

| $A-\underset{\underset{O}{\|}}{C}-$ | $R_3$ | M.p. (°C.) B.p. (p) | Process according to |
|---|---|---|---|
| thiophene-C(=O)- | 2-chlorophenyl | 50 | B |
| thiophene-C(=O)- | 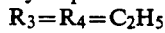 (2-methylthiophene, CH₃) | 103 | B |
| thiophene-C(=O)- | 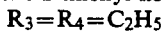 (CH₃-thiophene-CH₃) | Oil≠ | B |

*$R_f$ = 0.23 (CH₂Cl₂/cyclohexane - 1/1)
≠$R_f$ = 0.3 (CH₂Cl₂/cyclohexane - 1/1)

C) α) Ethyl 3-ethyl-2-pentenoate formula XVI:
$R_3 = R_4 = C_2H_5$

Add a solution of 74 g of ethyl diethylphosphonoacetate in 200 ml of tetrahydrofuran dropwise, at a temperature of 10° to 15° C., to 15.5 g of sodium hydride in suspension in 100 ml of tetrahydrofuran.

After the end of the addition, stir for 1 hour at room temperature and then cool to a temperature below 15° C. before adding a solution of 28 g of 3-pentanone in 200 ml of tetrahydrofuran while maintaining the temperature at less than 15° C. Then leave at room temperature for 12 hours and then pour the reaction medium into one litre of saturated aqueous ammonium chloride solution. Extract the aqueous phase with diethyl ether. Concentrate the ether extracts, washed with salted water and dried. The oil obtained is used as it is in the following stage.

Quantitative yield.

β) 3-Ethyl-2-pentenoic acid formula XV:
$R_3 = R_4 = C_2H_5$

Add 35 g of potassium hydroxide in solution in 200 ml of water to a solution in 300 ml of methanol of 49 g of the oil obtained in α and leave stirring at room temperature for 12 hours. Then introduce 100 ml of water into the reaction mixture and extract the aqueous alcoholic phase with diethyl ether. Acidify the separated aqueous phase with the addition of 10 N sulphuric acid while cooling and extract it with diethyl ether. Concentrate the ether extracts, washed with salted water and dried. The acid required is thus isolated in the oily form.

Yield: 66%.

γ) 2-Ethyl-1-butylene 2-thienyl ketone formula XIV:
$R_3 = R_4 = C_2H_5$

Add 33.6 g of thiophene to a solution of 18.8 g of the acrylic acid (XV: $R_3 = R_4 = C_2H_5$) in 40 ml of dichloromethane and introduce the mixture over 20 minutes into 100 g of polyphosphoric acid at 35° C. After one hour at this temperature, pour the reaction mixture into ice-cold water and then extract the aqueous phase with dichloromethane.

Concentrate the dried organic extracts and purify the residual oil by chromatography on a silica column (eluent: toluene) and then by distillation B.p. = 132° C. (at 2000 Pa).

Yield: 65%.

PREPARATION OF CONDENSED CYCLOPENTANONES

D)
4-(2-Chlorophenyl)-4-methylthieno[2,3-b]cyclopentan-6-one (Scheme a) formula II: A=thiophene; $R_3=CH_3$; $R_4$=2-chlorophenyl α) Ethyl 2-cyano-3-(3-thienyl)-2-butenoate: formula IX: A=3-thienyl; $R_3=CH_3$ Heat a mixture of 19.3 g of 3-acetylthiophene, 14.15 g of ethyl cyanoacetate, 1.9 g of ammonium acetate and 6 g of acetic acid in 50 ml of toluene while removing the water as fast as it is formed by azeotropic distillation (Dean & Stark apparatus). After 8 hours, cool the reaction mixture and introduce therein 50 ml of water and 100 ml of diethyl ether. Separate the organic phases, wash them with salted water and dry over anhydrous magnesium sulphate. Evaporate the solvent to dryness and distil the oil under vacuum:

B.p. 140° C. (at 80 Pa). The required product crystallises.

M.p. = 80° C.

Yield: 78%.

β) Ethyl 3-(2-chlorophenyl)2-cyano-3-(3-thienyl)butanoate formula X: A=3-thienyl; $R_3=CH_3$; $R_4$=2-chlorophenyl Add, under argon, a third of the volume of a solution of 15 g of 2-bromo-1-chlorobenzene in 50 ml of dry diethyl ether to 2 g of magnesium turnings in suspension in 5 ml of dry ethyl ether, then add a crystal of iodine to the reaction mixture and heat the mixture on a waterbath. When the magnesium has started reacting, add the remaining solution of 2-bromo-1-chlorobenzene dropwise. Maintain at reflux until the magnesium in the reaction mixture has completely disappeared. Add, after cooling the reaction mixture and while maintaining the temperature between 15° C. and 20° C., a solution of 17.5 g of ethyl 2-cyano-3-(3-thienyl)-2-butenoate, prepared in the preceding stage α, to 400 ml of diethyl ether. At the end of the addition, leave the reaction mixture stirring at room temperature overnight and then introduce therein 50 ml of a 1 N aqueous hydrochloric acid solution. After 10 minutes, separate the ether phase, wash it with ice-cold water and dry it over anhydrous sodium sulphate and then evaporate the solvent; purify the residual oil by flash chromatography on a silica column, eluting with toluene.

Yield: 80%. Yellow oil.

TLC (SiO$_2$): R$_f$=0.7 (toluene-ethyl acetate 97/3).

The products listed in Table 2 were prepared according to the same process; they are oils, except when otherwise mentioned.

TABLE 2

| A | R$_3$ | R$_4$ | Yield % | TLC (SiO$_2$) R$_f$(eluent) v/v |
|---|---|---|---|---|
|  | CH$_3$ |  | 72 | 0.6 (toluene/AcOEt) 9/1 |
| " | " |  CH$_3$O | 78 | 0.42 (toluene/AcOEt) 96/4 |
| " | " |  Cl | 80 | 0.7 (toluene/AcOEt) 97/3 |
| " | " |  Br | 68 | 0.3 (CH$_2$Cl$_2$/cyclohexane) 1/1 |
| " | " | C$_2$H$_5$ | 80 | 0.4 (CH$_2$Cl$_2$/cyclohexane) 1/1 |
| " | " |  | 72 | 0.5 (toluene/AcOEt) 95/5 M.p. = 66° C. |
| " | H |  | 76 | 0.4 (toluene) |
| " | H |  | 97 | 0.4 (toluene/AcOEt) 97/3 |
| " | " |  OCH$_3$ | 80 | 0.4 (toluene/AcOEt) M.p. = 116° C. |

TABLE 2-continued

| A | R$_3$ | R$_4$ | Yield % | TLC (SiO$_2$) R$_f$(eluent) v/v |
|---|---|---|---|---|
|  | CH$_3$ |  Cl | 80 | 0.6 (CH$_2$Cl$_2$/cyclohexane) 8/2 |
|  | CH$_3$ |  CH$_3$ | 30 | 0.6 (toluene/AcOEt) 96/4 |
| " | " | Cl—— | 40 | 0.3 (cyclohexane/isopropyl ether) 50/50 |
| " | " |  Cl | 49 | 0.3 (toluene) |
| " | " |  | 10 | 0.6 (CH$_2$Cl$_2$) |

AcOEt = ethyl acetate

γ) 3-(2-Chlorophenyl)-3-(3-thienyl)butanoic acid
formula XI: A=3-thienyl; R$_3$=CH$_3$;
R$_4$=2-chlorophenyl Rapidly add 14.7 g of potassium hydroxide pellets and then 3.8 ml of water to a solution in 130 ml of ethylene glycol of 11.5 g of ethyl 3-(2-chlorophenyl)-2-cyano-3-(3-thienyl)butanoate prepared according to β. Heat the mixture at reflux for 48 hours. After cooling, filter the insoluble material and pour the filtrate into one volume of water; wash three times with 50 ml of diethyl ether and then acidify the aqueous phase by addition of 10N hydrochloric acid until the pH=4, before extracting with diethyl ether. Concentrate the dried ether extracts to dryness. Purify the residue by filtration on a silica bed while eluting with CH$_2$Cl$_2$/CH$_3$OH (9/1).

Oil, R$_f$=0.5 (CH$_2$Cl$_2$/CH$_3$OH - 9/1).

Yield: 93%.

Other acids XI which were prepared according to the same process are described in Table 3.

TABLE 3

| A | R$_3$ | R$_4$ | Yield % | TLC R$_f$(eluent) v/v |
|---|---|---|---|---|
|  | CH$_3$ |  | 94 | 0.3 (CH$_2$Cl$_2$/CH$_3$OH) 96/4 |
| " | " |  CH$_3$O | 75 | 0.5 (CH$_2$Cl$_2$/C$_2$H$_5$OH) 95/5 |

TABLE 3-continued structure: A ring with $R_3$, $R_4$ substituents on carbon, CH2-COOH chain

| A | $R_3$ | $R_4$ | Yield % | TLC $R_f$(eluent) v/v |
|---|---|---|---|---|
| " | " | 2-Cl-phenyl | 93 | 0.5 (CH$_2$Cl$_2$/CH$_3$OH) 9/1 |
| " | " | 2-Br-phenyl | 85 | 0.4 (CH$_2$Cl$_2$/CH$_3$OH) 96/4 |
| " | " | C$_2$H$_5$ | 98 | 0.5 (CH$_2$Cl$_2$/CH$_3$OH) 9/1 |
| " | " | cyclohexyl | 88 | 0.5 (CH$_2$Cl$_2$/CH$_3$OH) 9/1 M.p. = 73° C. |
| " | H | 2-OCH$_3$-phenyl | 88 | 0.5 (CH$_2$Cl$_2$/CH$_3$OH) 95/5 M.p. = 130° C. |
| " | H | cyclohexyl | 71 | 0.56 (CH$_2$Cl$_2$/C$_2$H$_5$OH) 95/5 |
| " | " | 2-thienyl | 77 | 0.5 (CH$_2$Cl$_2$/CH$_3$OH) 95/5 M.p. = 123° C. |
| 2-thienyl | CH$_3$ | 2-Cl-phenyl | 86 | 0.5 (CH$_2$Cl$_2$/CH$_3$OH) 96/4 |
| 3-thienyl | CH$_3$ | 2-CH$_3$-phenyl | 85 | 0.5 (CH$_2$Cl$_2$/CH$_3$OH) 95/5 |
| " | " | 4-Cl-phenyl | 90 | 0.5 (CH$_2$Cl$_2$/CH$_3$OH) 9/1 |
| " | " | 3-Cl-phenyl | 92 | 0.5 (CH$_2$Cl$_2$/CH$_3$OH) 9/1 |
| " | " | cyclopentyl | 90 | 0.4 (CH$_2$Cl$_2$/CH$_3$OH) 95/5 |

δ)
4-(2-Chlorophenyl)-4-methylthieno[2,3-b]cyclopentan-6-one formula II: A=thiophene; $R_3$=CH$_3$; $R_4$=2-chlorophenyl Slowly add, with mechanical stirring, 43 g of 3-(2-chlorophenyl)-3-(3-thienyl)butanoic acid prepared according to the process γ in solution in 120 ml of toluene to 360 g of polyphosphoric acid which has been preheated to 90° C. Stir the reaction medium at 110° C. for 8 hours, bring it back to room temperature and add 1000 ml of ice-cold water and then 1000 ml of ethyl acetate; after stirring vigorously for 15 minutes, separate the organic phase. Purify the oil, obtained after evaporation of the solvent from this washed and dried phase, by chromatography on a silica column (eluent: dichloromethane).

$R_f$=0.5 (CH$_2$Cl$_2$).
Yield: 87%.

Ketones prepared according to this process are described in Table 4; they are oils.

TABLE 4

Formula II: bicyclic structure with A ring fused to cyclopentanone bearing $R_3$, $R_4$

| A | $R_3$ | $R_4$ | Yield % | TLC (SiO$_2$) $R_f$(eluent) v/v |
|---|---|---|---|---|
| 2-thienyl | CH$_3$ | phenyl | 80 | 0.4 (CH$_2$Cl$_2$/cyclohexane) 8/2 |
| " | " | 2-OCH$_3$-phenyl | 71 | 0.44 (toluene) |
| " | " | 2-Cl-phenyl | 87 | 0.5 (CH$_2$Cl$_2$) |
| " | " | 2-Br-phenyl | 87 | 0.3 (CH$_2$Cl$_2$/cyclohexane) 8/2 |
| " | " | C$_2$H$_5$ | 72 | 0.3 (CH$_2$Cl$_2$/CH$_3$OH) 9/1 |
| " | " | cyclohexyl | 96 | 0.4 (toluene/AcOEt) 97/3 |
| " | H | 2-OCH$_3$-phenyl | 70 | 0.4 (CH$_2$Cl$_2$/cyclohexane) 95/5 |
| " | " | 2-thienyl | 77 | 0.4 (toluene/AcOEt) 94/6 |
| " | " | cyclohexyl | 86 | 0.54 (CH$_2$Cl$_2$) |
| 2-thienyl (S-substituted) | CH$_3$ | 2-Cl-phenyl | 78 | 0.4 (CH$_2$Cl$_2$/cyclohexane) 8/2 |

E) 4-(2-Thienyl)thieno[2,3-b]cyclopentan-6-one formula II: A=thiophene; $R_3$=H; $R_4$=2-thienyl Add 1 ml of dimethylformamide and then, dropwise, 1 ml of oxalyl chloride to a solution of 1 g of 3-(2-thienyl)-3-(3-thienyl)propanoic acid in 15 ml of dry toluene. Stir the reaction mixture for 4 hours at room temperature, evaporate the toluene and dissolve the residue obtained in 16 ml of dry dichloromethane.

Add a solution of 0.6 ml of SnCl$_4$ dissolved in 2 ml of dry dichloromethane dropwise to this solution at 0° C. and then stir for 1 h 30. Then pour the reaction mixture onto 2 g of ice and 2 ml of water, separate the organic phase, wash it with 3N hydrochloric acid and then with water and dry it. Purify the residue, obtained after evaporation, by flash chromatography on a silica column (eluent: toluene/ethyl acetate-94/6). Oil: yield 67%.

F) 4,4-Dimethylthieno[2,3-b]cyclopentan-6-one formula II: $R_3=R_4=CH_3$; A=thiophene Add, in portions, 15 g of the chalcone XIV ($R_3=R_4=CH_3$; A=2-thienyl) to 75 g of polyphosphoric acid which has been preheated to 80° C. and then stir the mixture at 110° C. for 4 hours. After cooling, add 500 g of ice to the reaction mixture and extract the aqueous phase with ethyl acetate. Evaporate the organic extracts, dried residual oil by flash chromatography on a silica column (eluent: dichloromethane).

Yield: 78% - oil.
TLC: $R_f=0.5$ (toluene).

4,4-Diethylthieno[2,3-b]cyclopentan-6-one formula II: A=thiophene; $R_3=R_4=C_2H_5$ is obtained according to the same process.

Yield: 45%—oil—
TLC: $R_f=0.6$ ($CH_2Cl_2$).

G) 4-(2-Chlorophenyl)thieno[2,3-b]cyclopentan-6-one (formula II; A=thiophene; $R_4$=2-chlorophenyl; $R_3$=H)

Introduce 200 g of polyphosphoric acid (PPA) and 350 ml of toluene into a 1 l round-bottom flask with stirring and in a nitrogen atmosphere. Heat to 100° C. Add a solution of 50 g of suitable chalcone in 150 ml of toluene over 15 min. Heat at reflux of the toluene for 3 hours 30 minutes, let the mixture return to about 40° C. and introduce a mixture of 200 g of ice and 50 ml of water into the mixture. Separate. Wash the organic phase with 3×250 ml of water. Dry over sodium sulphate and then remove the toluene under reduced pressure. Take up the residue in 500 ml of isopropyl ether. Heat at reflux. Add 3 g of charcoal. Filter while hot. Leave to crystallise at room temperature and then cool to 0° C. Filter. Dry under reduced pressure at 30° C.

30.6 g of the required product are thus obtained which melts at 104° C. A second crop of 4 g is obtained by concentrating the isopropyl ether solution by half.

The compounds of Table 5 were prepared by applying method G:

TABLE 5

| A–C(=O)– | $R_4$ | M.p. | TLC ($SiO_2$): $R_f$(eluent) V/V | Yield (%) |
|---|---|---|---|---|
| 2-thienyl-C(=O)– | —$CH_3$ | oil | 0.4 ($CH_2Cl_2$) | 68 |
| " | —$C(CH_3)_3$ | oil | 0.35 ($CH_2Cl_2$/cyclohexane) 8/2 | 65 |
| " | phenyl | 83° C. | — | 60 |
| " | 2-chlorophenyl | 104° C. | — | 65 |
| " | 3-chlorophenyl | 75° C. | — | 58 |
| " | 4-chlorophenyl | 69° C. | — | 60 |

TABLE 5-continued
| A | R3 / R4 | | II |
|---|---|---|---|
| | 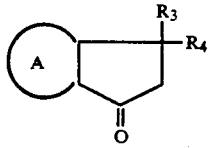 | 92° C. — | 64 |
| " | 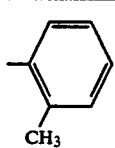 | 90° C. — | 70 |
| " | 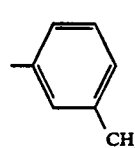 | 105° C. — | 71 |
| " | 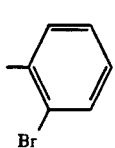 | 82° C. — | 45 |
| 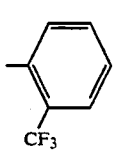 | 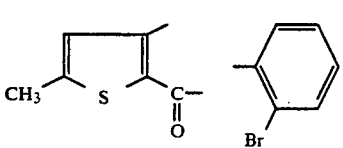 | 112° C. — | 67 |
| " | 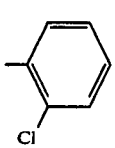 | 93° C. — | 88 |
| 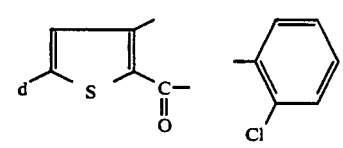 | 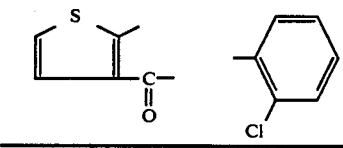 | oil  0.1 (CH₂Cl₂/cyclohexane) 1/1 | 91 |
| 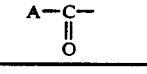 | 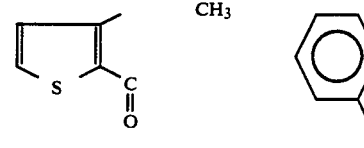 | 152° C. — | 89 |
| A—C(=O)— | R3 | R4 | Yield % | TLC (SiO₂) R$_f$(eluent) v/v |
|---|---|---|---|---|
| (thiophene-C(=O)—) | CH₃ | (dimethylphenyl) | 46 | 0.5 (CH₂Cl₂) |

TABLE 5-continued

| | | II | | |
|---|---|---|---|---|
| " | " | (4-Cl-phenyl) | 95 | 0.4 (CH$_2$Cl$_2$) |
| " | " | (3-Cl-phenyl) | 68 | 0.3 (cyclohexane/isopropyl ether) 50/50 |
| " | " | (cyclopentyl-dimethyl) | 79 | 0.4 (CH$_2$Cl$_2$) |
| " | H | (2-OH-phenyl) | 61 | 0.3 (CH$_2$Cl$_2$/CH$_3$OH) 97/3 |
| " | " | (2-OC$_2$H$_5$-phenyl) | 63 | 0.5 (CH$_2$Cl$_2$/CH$_3$OH) 97/3 |
| " | " | (2-OC$_3$H$_7$-phenyl) | 89 | 0.5 (CH$_2$Cl$_2$/CH$_3$OH) 95/5 |

PREPARATION OF AN ETHER OF ACETONE OXIME

H) Acetone oxime O-(2-(N,N-dimethylamino)ethyl) ether (formula VII: $R_a=R_b=CH_3$; $Q=(CH_2)_2$; $R_1=R_2=CH_3$)

Introduce 149.2 g of acetone oxime, 345.72 g of N,N-dimethyl-2-chloroethylamine hydrochloride, 2.5 l of toluene and 45 g of Aliquat ® 336 (quaternary ammonium phase transfer catalyst marketed by Aldrich) under nitrogen into a 4 l round-bottom flask. Stir at room temperature and add 636 g of K$_2$CO$_3$. Heat progressively to reflux and maintain heating for 18 hours and then cool to room temperature. Add 1.5 l of water. Separate. Wash the organic phase 2 times with 1 l of water and dry it over magnesium sulphate. Remove the toluene by distillation under reduced pressure. Take up the residue in 600 ml of acetone and add a solution of 180 g of oxalic acid in 850 ml of acetone.

After stirring for 10 minutes at room temperature, filter the precipitate formed. Rinse it with acetone and dry it under reduced pressure. 189.5 g of the H-oxalate of the required product are thus obtained, which melts at 128° C.

A second crop of 50 g is obtained after introducing oxalic acid into the toluene distillate.

PREPARATION OF O-SUBSTITUTED HYDROXYLAMINES

I) O-(2-(N,N-Dimethylamino)ethyl)hydroxylamine (formula III: $Q=(CH_2)_2$; $R_1=R_2=CH_3$)

Dissolve 60 g of the salt of the ether of acetone oxime obtained in H) in 260 ml of water into which 110 ml of a concentrated aqueous hydrochloric acid solution has been introduced.

Maintain the solution for 11 hours at its reflux temperature and then remove the acetone by distillation before concentrating under reduced pressure at 55° C. Dissolve the residue in a mixture of 160 ml of isopropanol, 160 ml of ethyl ether and 160 ml of acetonitrile and isolate the white precipitate.

58 g of the dihydrochloride of the final product are thus obtained, melting between 160° C. and 170° C.

J) O-(2-Bromoethyl)hydroxylamine (formula IV: Q=(CH$_2$)$_2$; X=Br)

a) N-(2-Bromoethoxy)phthalimide

Dissolve 32.6 g of N-hydroxyphthalimide in 240 ml of dimethylformamide and introduce, into this solution, 74 g of 1,2-dibromoethane and then 40 g of triethylamine. Stir the reaction mixture at room temperature for 20 hours and then filter the crystals which have precipitated. Pour the filtrate into 1500 ml of cold water and isolate the white precipitate formed. After washing with water and drying in an oven, the product is obtained, with a 60% yield, which melts at 98° C.

b) O-(2-Bromoethyl)hydroxylamine

Suspend the crystals of N-(2-bromoethoxy)phthalimide obtained in a) in 80 ml of concentrated acetic acid and add 115 ml of 48% hydrobromic acid. Maintain the reaction mixture at reflux until it has completely dissolved (10 minutes) and let it return to room temperature and then cool at 0° C. for 1 hour. Separate the phthalic acid crystals which have appeared and evaporate the filtrate to dryness. Solidify the oily residue obtained in diethyl ether; white crystals of O-(2-bromoethyl)hydroxylamine hydrobromide are obtained with a 60% yield.
M.p.=190° C.

EXAMPLE 1

4-(2-Chlorophenyl)Thieno[2,3-B]Cyclopentan-6-One Oxime O-(2-{N,N-Dimethylamino}Ethyl) ether (Formula I: A=Thiophene: R$_3$=2-Chlorophenyl: R$_4$=H: Q=CH$_2$Ch$_2$; R$_1$=R$_2$=CH$_3$), by Transoximation Introduce 89.4 g of 4-(2-chlorophenyl)thieno[2,3-b]cyclopentan-6-one and 95 g of acetone oxime O-(2-(N,N-dimethylamino)ethyl) ether into 600 ml of n-butanol. Add a mixture of 200 ml of n-butanol, 40 ml of concentrated sulphuric acid and 51 ml of water. Continuously distil the water/n-butanol azeotrope from the mixture while adding a water/n-butanol mixture (40/60-v/v) in order to keep the volume constant. After 8 hours, return to room temperature, add 300 ml of water and separate the organic phase; after washing with water, remove the solvent under reduced pressure. Pour 800 ml of isopropyl ether and 400 ml of water onto the mixture as well as a 1N aqueous NaOH solution to a pH of 10. Separate the organic phase and evaporate the solvent after washing and drying.

Dissolve the residual oil in 550 ml of acetone and add 32.4 g of oxalic acid in solution in 200 ml of acetone. Isolate the H-oxalate precipitate obtained. W=137 g. M.p.=140° C.

It contains approximately 70% of the Z isomer and 30% of the E isomer (determination by high pressure liquid chromatography).

EXAMPLE 2

4-(2-Chlorophenyl)Thieno[2,3-B]Cyclopentan-6-One Oxime O-(2-(N,N-Dimethylamino}Ethyl) Ether by Reacting with O-Alkylhydroxylamine Dissolve 1 g of 4-(2-chlorophenyl)thieno[2,3-b]cyclopentan-6-one in 20 ml of methanol and introduce 1.12 g of O-(2-(N,N-dimethylamino)ethyl)hydroxylamine hydrochloride and then 0.45 ml of acetic acid and 0.65 ml of pyridine into the solution. Maintain the mixture at its reflux temperature for 12 hours. Concentrate, pour 100 ml of ethyl acetate onto the residue, wash with 20 ml of a 0.1N aqueous NaOH solution, then with water and dry.

Remove the solvent under reduced pressure and chromatograph the residue on a silica column by eluting with a mixture of methylene chloride and methanol (9/1 - v/v)

The H-oxalate of the final product is a mixture of the 2 geometric isomers, comprising 70% of Z isomer, and melts at 140° C.

The isomers are separated by high performance liquid chromatography on a Porasil ® column marketed by Waters by eluting with a mixture of ethyl acetate/isopropyl ether/triethylamine (50/50/0.5-v/v/v). The H-oxalate of the Z isomer melts at 124° C., the H-fumarate of the E isomer at 144° C.

Formula XVI schematically represents the position of the substituent on the oxygen for this E isomer (trans with respect to A, around C=N.

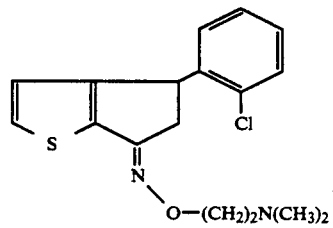

EXAMPLE 3

4-Phenyl-4-Methylthieno[2,3-B]Cyclopentan-6-One Oxime O-(2-(N,N-Dimethylamino}Ethyl) Ether:

a) 4-Phenyl-4-methylthieno[2,3-b]cyclopentan-6-one oxime O-(2-bromoethyl) ether (Formula V: A=Thiophene; R$_3$=CH$_3$; R$_4$=Phenyl; Q=CH$_2$CH$_2$; X=Br)

Dissolve 1.1 g of 4-methyl-4-phenylthieno[2,3-b]cyclopentan-6-one (II: A=thiophene; R$_3$=CH$_3$; R$_4$=phenyl) in 40 ml of absolute ethanol and successively add 2.1 g (0.0096 mole) of 2-(bromoethyl)hydroxylamine and then 0.6 ml of glacial acetic acid and 0.66 ml of dry pyridine, before maintaining the reaction mixture at reflux for 3 hours. Evaporate to dryness at the end of the reaction and treat the residue with a mixture of water and ethyl acetate. Isolate the organic phase and extract the aqueous phase with ethyl acetate. Dry and concentrate the organic extracts to dryness to obtain an oily residue consisting of the mixture of the two racemic E and Z stereoisomers (80/20)

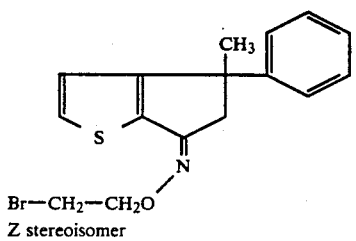

Z stereoisomer

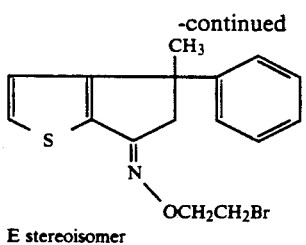

E stereoisomer

Each stereoisomer is isolated by flash chromatography on a silica column (eluent: dichloromethane/cyclohexane - 1/1).

Z stereoisomer: oil; $R_f$=0.30 ($CH_2Cl_2$/cyclohexane-6/4); yield: 65% with respect to the ketone.

E stereoisomer: oil; $R_f$=0.61 ($CH_2Cl_2$/cyclohexane-6/4); yield: 22% with respect to the ketone.

b) Z and E stereoisomers of 4-methyl-4-phenylthieno[2,3-b]cyclopentan-6-one oxime O-(2-{N,N-dimethylamino}ethyl) ether (formula I: A=thiophene; Q=$CH_2CH_2$; $R_1$=$R_2$=$CH_3$; $R_3$=$CH_3$; $R_4$=phenyl)

Dissolve 0.5 g of the Z or E brominated alkoxime obtained according to a) in 15 ml of dimethylformamide; add an excess (5 equivalents) of gaseous dimethylamine at room temperature; leave at room temperature for 24 hours and then pour into water and extract the aqueous phase with ethyl acetate. Dry the organic extracts over anhydrous sodium sulphate and evaporate to dryness. Purify the oily residue by flash chromatography on a silica column (eluent: dichloromethane/methanol - 92/8).

Preparation of the oxalate: addition of one equivalent of oxalic acid dissolved in the minimum amount of acetone to a solution of the oxime ether obtained dissolved in 5 ml of acetone, and filtration of the crystals of the oxalate obtained.

Z stereoisomer: M.p.(H-oxalate): 101° C., yield: 90%
E stereoisomer: M.p.(H-oxalate): 176° C., yield: 88%

The compounds mentioned in the following Table 6 were prepared by applying one of the abovementioned processes.

TABLE 6

| Examples | (A)—C=N— | Q | $NR_1R_2$ | $R_3$ | $R_4$ | M.p. (°C.) (H-oxalate) | % Z* | % E* |
|---|---|---|---|---|---|---|---|---|
| 4 | thiophene-C=N | $CH_2CH_2$ | —N($CH_3$)$_2$ | H | —$CH_3$ | 116° C. | 100 | 0 |
| 5 | " | $CH_2CH_2$ | —N($CH_3$)$_2$ | H | —$CH_3$ | 150° C. | 0 | 100 |
| 6 | " | $CH_2CH_2$ | —N($CH_3$)$_2$ | H | —$CH_3$ | 124° C. | 57 | 43 |
| 7 | " | $CH_2CH_2$ | —N($CH_3$)$_2$ | H | —C($CH_3$)$_3$ | 127° C. | 100 | 0 |
| 8 | " | $CH_2CH_2$ | —N($CH_3$)$_2$ | H | —C($CH_3$)$_3$ | 151° C. | 0 | 100 |
| 9 | " | $CH_2CH_2$ | —N($C_2H_5$)$_2$ | H | Cl-phenyl | 129° C. | 100 | 0 |
| 10 | " | $CH_2CH_2$ | —N($C_2H_5$)$_2$ | H | Cl-phenyl | 148° C. | 0 | 100 |
| 11 | " | $CH_2CH_2$ | —N-piperidine | H | Cl-phenyl | 156° C. | 100 | 0 |

TABLE 6-continued
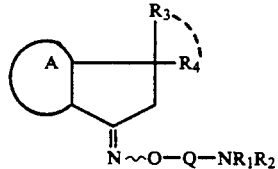
I
| Examples | 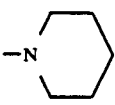 | Q | NR₁R₂ | R₃ | R₄ | M.p. (°C.) (H-oxalate) | % Z* | % E* |
|---|---|---|---|---|---|---|---|---|
| 12 | " | CH₂CH₂ | 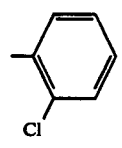 | H | 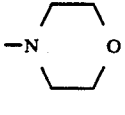 | 169° C. | 0 | 100 |
| 13 | " | CH₂CH₂ | 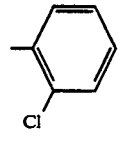 | H | 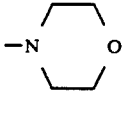 | 105° C. | 100 | 0 |
| 14 | " | CH₂CH₂ | 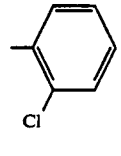 | H | 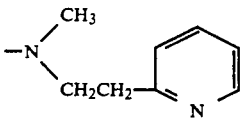 | 183° C. | 0 | 100 |
| 15 | " | CH₂CH₂ | 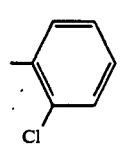 | H | 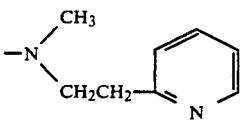 | 140° C. | 100 | 0 |
| 16 | " | CH₂CH₂ | 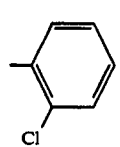 | H | 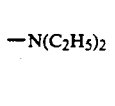 | 154° C. | 0 | 100 |
| 17 | " | CH₂CH₂ | —N(C₂H₅)₂ | H | 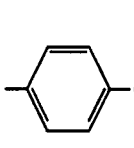 | 155° C. | 70 | 30 |
| 18 | " | CH₂CH₂ | 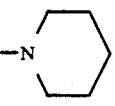 | H | 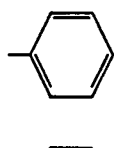 | 152° C. | 70 | 30 |
| 19 | " | CH₂CH₂ | 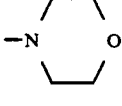 | H | 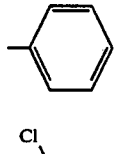 | 144° C. | 70 | 30 |
| 20 | " | CH₂CH₂CH₂ | —N(CH₃)₂ | H |  | 142° C. | 70 | 30 |

TABLE 6-continued

I

| Examples | [A]-C(=N-) | Q | NR₁R₂ | R₃ | R₄ | M.p. (°C.) (H-oxalate) | % Z* | % E* |
|---|---|---|---|---|---|---|---|---|
| 21 | " | CH₂CH₂ | —N(CH₃)₂ | H | 2-Cl-C₆H₄ | 124° C. | 100 | 0 |
| 22 | " | CH₂CH₂ | —N(CH₃)₂ | H | 2,3-Cl₂-C₆H₃ | 144° C. | 0 | 100 |
| 23 | " | CH₂CH₂ | —N(CH₃)₂ | H | C₆H₅ | 100° C. | 70 | 30 |
| 24 | " | CH₂CH₂ | —N(CH₃)₂ | H | 2-Br-C₆H₄ | 78° C. | 100 | 0 |
| 25 | " | CH₂CH₂ | —N(CH₃)₂ | H | 2-Br-C₆H₄ | 182° C. | 0 | 100 |
| 26 | " | CH₂CH₂ | —N(CH₃)₂ | H | 2-Br-C₆H₄ | 129° C. | 70 | 30 |
| 27 | " | CH₂CH₂ | —N(CH₃)₂ | H | 2-CH₃-C₆H₄ | 116° C. | 70 | 30 |
| 28 | 3-methyl-thiophen-2-yl C(=N-) | CH₂CH₂ | —N(CH₃)₂ | H | 2-CF₃-C₆H₄ | 153° C. | 100 | 0 |
| 29 | " | CH₂CH₂ | —N(CH₃)₂ | H | 2-CF₃-C₆H₄ | 155° C. | 0 | 100 |

TABLE 6-continued

| Examples | [A=C=N-] | Q | NR₁R₂ | R₃ | R₄ | M.p. (°C.) (H-oxalate) | % Z* | % E* |
|---|---|---|---|---|---|---|---|---|
| 30 | " | CH₂CH₂ | —N(CH₃)₂ | H | 2-H₃CO-C₆H₄ | 114° C. | 100 | 0 |
| 31 | " | CH₂CH₂ | —N(CH₃)₂ | H | 2-H₃CO-C₆H₄ | 164° C. | 0 | 100 |
| 32 | " | CH₂CH₂ | —N(CH₃)₂ | H | 2-H₃CO-C₆H₄ | 120° C. | 55 | 45 |
| 33 | " | CH₂CH₂ | —N(CH₃)₂ | H | 3-Cl-C₆H₄ | 133° C. | 70 | 30 |
| 34 | " | CH₂CH₂ | —N(CH₃)₂ | H | 4-Cl-C₆H₄ | 151° C. | 70 | 30 |
| 35 | " | CH₂CH₂ | —N(CH₃)₂ | H | 3-CH₃-C₆H₄ | 168° C. | 70 | 30 |
| 36 | 5-methyl-3-methylthien-2-yl (H₃C-S-thiophene-CH₃) | CH₂CH₂ | —N(CH₃)₂ | H | 2-Cl-C₆H₄ | Oil (base) | 100 | 0 |
| 37 | " | CH₂CH₂ | —N(CH₃)₂ | H | 2-Cl-C₆H₄ | Oil (base) | 0 | 100 |
| 38 | " | CH₂CH₂ | —N(CH₃)₂ | H | 2-Cl-C₆H₄ | 167° C. | 70 | 30 |

TABLE 6-continued

Structure I: A-ring with R₃, R₄ substituents; =N~O—Q—NR₁R₂

| Examples | (A)—C(CH₃)=N— | Q | NR₁R₂ | R₃ | R₄ | M.p. (°C.) (H-oxalate) | % Z* | % E* |
|---|---|---|---|---|---|---|---|---|
| 39 | " | CH₂CH₂ | —N(CH₃)₂ | H | 2-Br-phenyl | 180° C. | 100 | 0 |
| 40 | " | CH₂CH₂ | —N(CH₃)₂ | H | 2-Br-phenyl | 168° C. | 0 | 100 |
| 41 | 5-Cl-3-methyl-thiophen-2-yl | CH₂CH₂ | —N(CH₃)₂ | H | 2-Cl-phenyl | 180° C. | 100 | 0 |
| 42 | " | CH₂CH₂ | —N(CH₃)₂ | H | 2-Cl-phenyl | 177° C. | 0 | 100 |
| 43 | 3-methyl-thiophen-2-yl | CH₂CH₂ | —NH₂ | H | 2-Cl-phenyl | 140° C. | 70 | 30 |
| 44 | " | CH₂CH₂ | —NHCH₃ | H | 2-Cl-phenyl | 168° C. | 100 | 0 |
| 45 | " | CH₂CH₂ | —NHCH₃ | H | 2-Cl-phenyl | 144° C. | 0 | 100 |
| 46 | 2-methyl-thiophen-3-yl | CH₂CH₂ | —N(CH₃)₂ | H | 2-Cl-phenyl | 189° C. | 100 | 0 |

TABLE 6-continued

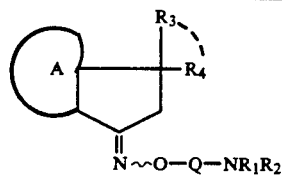

| Examples | A⟩C=N— | Q | NR₁R₂ | R₃ | R₄ | M.p. (°C.) (H-oxalate) | % Z* | % E* |
|---|---|---|---|---|---|---|---|---|
| 47 | 2-methyl-3-thienyl C=N | CH₂CH₂ | —N(CH₃)₂ | H | 2-chlorophenyl | 201° C. | 0 | 100 |
| 48 | 3-methyl-2-thienyl C=N | CH₂CH₂ | —N(CH₃)₂ | —CH₃ | 2-chlorophenyl | 108° C. | 90 | 10 |
| 49 | " | CH₂CH₂ | —N(CH₃)₂ | —CH₃ | 2-chlorophenyl | 130° C. | 0 | 100 |
| 50 | " | CH₂CH₂ | —N(CH₃)₂ | —CH₃ | 2-bromophenyl | 103° C. | 96 | 4 |
| 51 | " | CH₂CH₂ | —N(CH₃)₂ | —CH₃ | —CH₃ | 158° C. | 100 | 0 |
| 52 | " | CH₂CH₂ | —N(CH₃)₂ | —CH₃ | —CH₃ | 160° C. | 0 | 100 |
| 53 | " | CH₂CH₂ | —N(CH₃)₂ | —C₂H₅ | —C₂H₅ | 110° C. | 75 | 25 |
| 54 | " | CH₂CH₂ | —N(CH₃)₂ | CH₃ | —C₂H₅ | 121° C. | 96 | 4 |
| 55 | " | CH₂CH₂ | —N(CH₃)₂ | CH₃ | —C₂H₅ | 155° C. | 3 | 97 |
| 56 | " | CH₂CH₂ | —N(CH₃)₂ |  | cyclohexyl | 120° C. | 65 | 35 |
| 57 | 3-methyl-2-thienyl C=N | CH₂CH₂ | —N(CH₃)₂ | H | 2-methylthienyl | 170° C. (dihydrate) | 100 | 0 |
| 58 | " | CH₂CH₂ | —N(CH₃)₂ | H | 2-methylthienyl | 136° C. | 0 | 100 |
| 59 | " | CH₂CH₂ | —N(CH₃)₂ | H | 2-methylthienyl | 132° C. (hemihydrate) | 65 | 35 |

TABLE 6-continued $$\text{I}$$

Structure: A ring (A) fused to a 5-membered ring bearing $R_3$ and $R_4$ substituents, with =N~O—Q—NR$_1$R$_2$ group.

| Examples | (A)—C(=N—)— | Q | NR$_1$R$_2$ | R$_3$ | R$_4$ | M.p. (°C.) (H-oxalate) | % Z* | % E* |
|---|---|---|---|---|---|---|---|---|
| 60 | " | CH$_2$CH$_2$ | —N(CH$_3$)$_2$ | CH$_3$ | 2-CH$_3$O-phenyl | 130° C. H-fumarate) | 100 | 0 |
| 61 | " | CH$_2$CH$_2$ | —N(CH$_3$)$_2$ | CH$_3$ | 2-CH$_3$O-phenyl | Oil (base)** | 0 | 100 |
| 62 | " | CH$_2$CH$_2$ | —N(CH$_3$)$_2$ | H | cyclohexyl | Oil (base)** | 100 | 0 |
| 63 | " | CH$_2$CH$_2$ | —N(CH$_3$)$_2$ | H | cyclohexyl | Oil (base)** | 0 | 100 |
| 64 | " | CH$_2$CH$_2$ | —N(CH$_3$)$_2$ | H | 2-OH-phenyl | 85° C. | 100 | 0 |
| 65 | " | CH$_2$CH$_2$ | —N(CH$_3$)$_2$ | H | 2-OH-phenyl | 130° C. | 0 | 100 |
| 66 | " | CH$_2$CH$_2$ | —N(CH$_3$)$_2$ | H | 2-OC$_2$H$_5$-phenyl | 90° C. | 100 | 0 |
| 67 | " | CH$_2$CH$_2$ | —N(CH$_3$)$_2$ | H | 2-OC$_2$H$_5$-phenyl | 142° C. | 0 | 100 |
| 68 | " | CH$_2$CH$_2$ | —N(CH$_3$)$_2$ | H | 2-OC$_3$H$_7$-phenyl | 120° C. | 100 | 0 |

TABLE 6-continued

I

| Examples | (A)=C−N− | Q | NR₁R₂ | R₃ | R₄ | M.p. (°C.) (H-oxalate) | % Z* | % E* |
|---|---|---|---|---|---|---|---|---|
| 69 | " | CH₂CH₂ | −N(CH₃)₂ | H | 2-OC₃H₇-phenyl | 130° C. | 0 | 100 |
| 70 | " | CH₂CH₂ | −N(CH₃)₂ | H | cyclopentyl | 146° C. | 100 | 0 |
| 71 | " | CH₂CH₂ | −N(CH₃)₂ | H | cyclopentyl | 154° C. | 0 | 100 |
| 72 | " | CH₂CH₂ | −N(CH₃)₂ | −CH₃ | 2-CH₃-phenyl | 90° C. | 0 | 100 |
| 73 | " | CH₂CH₂ | −N(CH₃)₂ | −CH₃ | 2-CH₃-phenyl | 110° C. | 90 | 10 |
| 74 | " | CH₂CH₂ | −N(CH₃)₂ | −CH₃ | 4-Cl-phenyl | 126° C. | 96 | 4 |
| 75 | " | CH₂CH₂ | −N(CH₃)₂ | −CH₃ | 4-Cl-phenyl | 185° C. | 1 | 99 |
| 76 | " | CH₂CH₂ | −N(CH₃)₂ | −CH₃ | 3-Cl-phenyl | / 126° C. | 98 | 2 |
| 77 | " | (CH₂)₃ | −N(CH₃)₂ | −CH₃ | phenyl | 100° C. | 98 | 2 |
| 78 | " | (CH₂)₃ | piperidin-1-yl | −CH₃ | phenyl | 167° C. | 2 | 98 |

TABLE 6-continued

| Examples | ⓐ-C=N- | Q | NR₁R₂ | R₃ | R₄ | M.p. (°C.) (H-oxalate) | % Z* | % E* |
|---|---|---|---|---|---|---|---|---|
| 79 | " | (CH₂)₂ | O‾N— (morpholino) | —CH₃ | phenyl | 150° C. | 99 | 1 |
| 80 | " | (CH₂)₂ | ▷—NH— | —CH₃ | 2-methoxyphenyl | 160° C. | 90 | 10 |
| 81 | " | CH₂CH₂ | ▷—NH— | —CH₃ | 2-methoxyphenyl | 182° C. | 10 | 90 |
| 82 | " | CH₂CH₂ | —N(CH₃)₂ | —CH₃ | 2-methoxyphenyl | 120° C. | 0 | 100 |
| 82 bis | " | CH₂CH₂ | —N(CH₃)₂ |  | cyclohexyl-methyl | 140° C. | 100 | 0 |
| 82 ter | " | CH₂CH₂ | —N(CH₃)₂ |  | cyclohexyl-methyl | 172° C. | 0 | 100 |

*The relative percentages of Z and E isomers were determined by high performance liquid chromatography.
**61: $R_f = 0.67$ (CH₂Cl₂/C₂H₅OH-8/2)
**62: $R_f = 0.64$ (CH₂Cl₂/C₂H₅OH-8/2)
**63: $R_f = 0.67$ (CH₂Cl₂/C₂H₅OH-8/2)

EXAMPLE 83

4-(2-Chlorophenyl)Thieno[2,3-B]Cyclopentan-6-One Oxime O-(2-{N-Methylamino}Ethyl) Ether (Formula I: A=Thiophene; R₃=2-Chlorophenyl; R₄=H; Q=CH₂CH₂; R₁=CH₃; R₂=H)

a) 4-(2-Chlorophenyl)thieno[2,3-b]cyclopentan-6-one oxime O-(2-bromoethyl) ether (formula V: A=thiophene; Q=CH₂CH₂; X=Br; R₃=H; R₄=2-chlorophenyl)

Dissolve 0.6 g of 4-(2-chlorophenyl)thieno[2,3-b]cyclopentan-6-one in 15 ml of ethanol and add successively 0.3 ml of acetic acid, then 0.35 ml of pyridine and 1.1 g of O-(2-bromoethyl)hydroxylamine hydrobromide, before maintaining the reaction mixture at reflux for 3 hours. Evaporate to dryness and take up the residue in ethyl acetate. Wash this organic solution with water, dry it and evaporate the solvent to obtain an oil which is purified by flash chromatography on silica (dichloromethane eluent).

Yield 98%.

The product obtained consists of a mixture of 70% Z geometric isomer and 30% E geometric isomer.

b) Dissolve 0.71 g of 4-(2-chlorophenyl)thieno[2,3-b]cyclopentan-6-one oxime O-(2-bromoethyl) ether, obtained according to a), in 25 ml of dimethylformamide and cool the reaction mixture to −30° C. before adding an excess of methylamine (approximately 10 equivalents) dissolved in 5 ml of dimethylformamide. After 5 hours at this temperature, remove the solvents by distillation and take up the oily residue in ethyl acetate; wash the organic phase with water, dry it and remove the solvent. The H-oxalate prepared according to the standard process melts at 159° C. The salt consists of 75% Z isomer and 25% E isomer.

Yield 93%.

EXAMPLE 84

Laevorotatory Z Isomer of 4-(2-Chlorophenyl)Thieno[2,3-B]Cyclopentan-6-One Oxime O-(2-{N,N-Dimethylamino}Ethyl)Ether a) Dissolve 1.3 g of the base obtained according to Example 21 in 20 ml of acetone. Add 10 ml of a solution in acetone of 0.88 g of dextrorotatory dibenzoyltartaric acid. Filter the precipitate and dissolve it in 20 ml of methanol at reflux. Isolate the precipitate formed after bringing back to room temperature and redissolve it in the minimum amount of methanol at reflux. Filter the precipitate formed after bringing back to room temperature, in order to obtain 1 g of salt melting at 161° C. Recover the base from the salt in a dichloromethane/aqueous sodium bicarbonate solution mixture. It is a colourless oil, weighing 470 mg, which has $[\alpha]_D = -53.7$ (C=0.918; CH$_3$OH).

The H-oxalate, prepared in acetone, melts at 123° C.; $[\alpha]_D = -40.39$ (C=1.114; CH$_3$OH), and the hydrochloride melts at 165° C.; $[\alpha]_D = -52.37$ (C=1.054; CH$_3$OH).

b) Dissolve 18 g of the base obtained according to Example 2, comprising 70% of Z isomer, in 150 ml of acetone. Add 20.2 g of dextrorotatory dibenzoyltartaric acid (monohydrate). Isolate the precipitate and recrystallise it three times in methanol in order to obtain 10 g of the dibenzoyltartrate which melts at 161° C. Recover the base (5 g) and prepare the oxalate as in a) from the 5 g of oil obtained. Yield: 79%. This oxalate, which comprises less than 1% of the E isomer, is the laevorotatory enantiomer of the Z isomer.

EXAMPLE 85

Dextrorotatory Z Isomer of 4-(2-Chlorophenyl)Thieno[2,3-B]Cyclopentan-6-One Oxime O-(2-{N,N-Dimethylamino)Ethyl)Ether Concentrate the acetone solution obtained according to Example 84 b); add an aqueous sodium bicarbonate solution and dichloromethane, stir, settle out and separate the organic phase; after drying, remove the solvent from it by distillation. Dissolve the residual oil in 100 ml of acetoneandadd 12.6 g of laevorotatory dibenzoyltartaric acid (monohydrate). Separate the precipitate and recrystallise it two times in methanol.

9 g of the salt are thus isolated which melts at 61° C.; the base is recovered in the usual way by reaction with sodium bicarbonate in a water/dichloromethane mixture. It is an oil which has $[\alpha]_D = +52.85$ (C=0.852; CH$_3$OH).

The H-oxalate, prepared in acetone with a yield of 70% starting from the mixture, melts at 123° C.; $[\alpha]_D = +40.56$ (C=0.965; CH$_3$OH), and the hydrochloride melts at 165° C.; $[\alpha]_D = +52.01$ (C=1.015; CH$_3$OH).

EXAMPLE 86

Laevorotatory E Isomer of 4-(2-Chlorophenyl)Thieno[2,3-B]Cyclopentan-6-One Oxime O-(2-{N,N-Dimethylamino}Ethyl)Ether Dissolve 3.2 g of the laevorotatory Z isomer base obtained previously (Example 84) in 50 ml of n-butanol. Add 1.84 g of methanesulphonic acid and heat at 85° C. for 2 hours. Pour into 1 volume of water and add one volume of ethyl ether; separate the organic phase; alkalize the aqueous phase and extract the final product from it into ethyl ether. Separate the Z and E isomers by high performance chromatography on a Porasil ® column marketed by Waters by eluting with a mixture of ethyl acetate, isopropyl ether and triethylamine (50/50/0.5-v/v/v).

The H-oxalate of the laevorotatory E isomer thus isolated, prepared in acetone, melts at 162° C.; $[\alpha]_D = -3.56$ (C=1.038; CH$_3$OH).

EXAMPLE 87

Dextrorotatory E Isomer of 4-(2-Chlorophenyl)Thieno[2,3-B]Cyclopentan-6-One Oxime O-(2-{N,N-Dimethylamino}Ethyl)Ether Carry out the partial isomerisation of the dextrorotatory Z isomer obtained according to Example 85 by applying the process described in Example 86 and chromatographythe mixture obtained in order to isolate the required product.

Its H-oxalate melts at 162° C.; $[\alpha]_D = +3.67$ (C=0.952; CH$_3$OH).

Other stereoisomers isolated via the intermediary of the salts of each enantiomer of dibenzoyltartaric acid figure in Table 7 below; the rotatory power was determined from a methanol solution of the product with a concentration of about 1.

TABLE 7

Structure: thieno-cyclopentane with substituents R$_3$, R$_4$, and N—O—CH$_2$CH$_2$N(CH$_3$)$_2$

| Ex. | R$_3$ | R$_4$ | M.p. (H-oxalate) | % Z | % E | α$_D$ |
|---|---|---|---|---|---|---|
| 88 | H | 2-methoxyphenyl | 120° C. | 100 | 0 | +32.6 |
| 89 | H | 2-methoxyphenyl | 120° C. | 100 | 0 | −32.3 |
| 90 | CH$_3$ | 2-chlorophenyl | 166° C. | 100 | 0 | +126.6 |
| 91 | CH$_3$ | 2-chlorophenyl | 166° C. | 100 | 0 | −126.6 |
| 92 | CH$_3$ | phenyl | 109° C. | 100 | 0 | +3.85 |

TABLE 7-continued

[Structure: thieno-cyclopentane with =N—O—CH₂CH₂N(CH₃)₂, substituents R₃, R₄]

| Ex. | R₃ | R₄ | M.p. (H-oxalate) | % Z | % E | $\alpha_D$ |
|---|---|---|---|---|---|---|
| 93 | CH₃ | phenyl | 109° C. | 100 | 0 | −4.25 |
| 94 | CH₃ | 2-OCH₃-phenyl | 120° C. | 100 | 0 | +109.7 |
| 95 | CH₃ | 2-OCH₃-phenyl | 120° C. | 100 | 0 | −108.7 |

EXAMPLE 96

4-(2-Chlorophenyl)Thieno[2,3-B]Cyclopentan-6-One Oxime O-(2-{N,N,N-Trimethylammonio}Ethyl) Ether Bromide (Formula Ia: A=Thiophene; Q=CH₂CH₂; R₁=R₂=R₅=CH₃; R₃=H; R₄=2-Chlorophenyl)

Suspend 0.4 g of the Z or E stereoisomer of 4-(2-chlorophenyl)thieno[2,3-b]cyclopentan-6-one oxime O-(2-bromoethyl) ether (prepared according to Example 4a) in 10 ml of acetonitrile and add dropwise 0.0065 mole of trimethylamine as a 25% solution in water and then 15 ml of dimethylformamide. After 3 days at room temperature, remove the volatile products by distillation and take up the residue in dichloromethane. Wash with water, dry and concentrate the organic phase to dryness. Purify the oily residue obtained by chromatography on a silica column (eluent: methanol). The quaternary ammonium compound is obtained with a yield greater than 90%.

Z stereoisomer: oily amorphous product; yield=92%
E stereoisomer: M.p.=201° C.; yield=91%

We claim:

1. A compound of formula

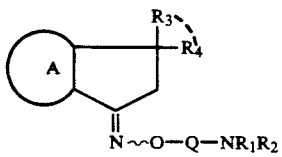

I in which A, which is a ring condensed with cyclopentane, represents a thiophene ring, unsubstituted or substituted with one or more groups chosen from (C₁-C₄) alkyl, (C₁-C₄) alkoxy, halo, nitro, hydroxyl and trifluoromethyl, Q represents a (C₂-C₄) alkylene R₁ and R₂, which are identical or different, represent H, (C₁-C₄) alkyl, pyridylethyl, or form, with the nitrogen atom to which they are bound, a saturated nitrogenous heterocyclic ring containing 5 to 7 atoms, optionally containing a heteroatom O, S or N, substituted or unsubstituted with (C₁-C₄) alkyl or phenyl, R₃ and R₄, which are identical or different, represent H, (C₁-C₄) alkyl, (C₄-C₈) cycloalkyl, trifluoromethyl or a phenyl, thienyl or furyl aromatic group, optionally carrying one or more substituents chosen from (C₁-C₄) alkyl, (C₁-C₄) alkoxy, halo, nitro, hydroxyl, trifluoromethyl, trifluoromethoxy, cyano, carboxyl, carbamoyl, N-(C₁-C₄)alkyl or N,N-(C₁-C₄)dialkylcarbamoyl and (C₁-C₄) alkoxycarbonyl, or R₃ and R₄, together with the carbon atom to which they are bound, form a (C₅-C₈) cycloalkyl, and their addition salts with an acid, and their quaternary ammonium derivatives, wherein the formula I represents each geometric isomer of the oxime group and each enantiomer due to the asymmetric carbon atoms or their mixtures in any proportion.

2. A compound according to claim 1, corresponding to the formula I in which A represents a thiophene, Q represents CH₂CH₂ and R₁ and R₂ independently represent H or alkyl.

3. A compound according to claim 1, corresponding to the formula I in which A represents a thiophene, Q represents CH₂CH₂, R₁ and R₂ independently represent H or CH₃ and R₃ and R₄ independently represent H, (C₁-C₄) alkyl or (C₄-C₈) cycloalkyl.

4. A compound according to claim 1, corresponding to the formula I in which A represents a thiophene, Q represents CH₂CH₂, R₁ and R₂ independently represent H or CH₃, R₃ represents H or CH₃ and R₄ represents phenyl optionally substituted with Cl, Br, F, OH, OCH₃ or CH₃.

5. A compound according to claim 1, corresponding to the formula I in which Q represents CH₂CH₂, R₁ and R₂ independently represent H or CH₃ and R₃ and R₄, together with the carbon atoms which carries them, form a (C₅-C₈) cycloalkyl group and A represents a thiophene.

6. Z isomer of a compound of claim 1.
7. Z isomer of a compound of claim 2.
8. Z isomer of a compound of claim 3.
9. Z isomer of a compound of claim 4.
10. Z isomer of a compound of claim 5.

11. A pharmaceutical composition, comprising one compound according to claim 1 as active ingredient, and a pharmaceutically acceptable carrier or vehicle.

12. A pharmaceutical composition, comprising one compound according to claim 2 as active ingredient, and a pharmaceutically acceptable carrier or vehicle.

13. A pharmaceutical composition, comprising one compound according to claim 3 as active ingredient, and a pharmaceutically acceptable carrier or vehicle.

14. A pharmaceutical composition, comprising one compound according to claim 4 as active ingredient, and a pharmaceutically acceptable carrier or vehicle.

15. A pharmaceutical composition, comprising one compound according to claim 5 as active ingredient, and a pharmaceutically acceptable carrier or vehicle.

16. A pharmaceutical composition, comprising one compound according to claim 6 as active ingredient, and a pharmaceutically acceptable carrier or vehicle.

* * * * *